United States Patent [19]
Grieser et al.

[11] 3,954,002
[45] May 4, 1976

[54] METHOD FOR CALIBRATING MOISTURE CONTENT MEASURING INSTRUMENTS

[75] Inventors: Frank Grieser, Lintorf; Rainer Klein, Duisburg, both of Germany

[73] Assignee: Mannesmann Aktiengesellschaft, Dusseldorf, Germany

[22] Filed: Mar. 29, 1973

[21] Appl. No.: 346,106

[30] Foreign Application Priority Data
Mar. 30, 1972 Germany............................ 2216379

[52] U.S. Cl. ..................................... 73/1 R; 73/73
[51] Int. Cl.² ........................................... G01T 3/00
[58] Field of Search................ 73/1 R, 73; 250/252, 250/302, 303

[56] References Cited
UNITED STATES PATENTS
2,526,636    10/1950    Colman.............................. 73/1 R

*Primary Examiner*—S. Clement Swisher
*Assistant Examiner*—Denis E. Corr
*Attorney, Agent, or Firm*—Ralf H. Siegemund

[57] ABSTRACT

Moisture testing instruments for use in heaped, loose material include a neutron source and a detector. The instrument is calibrated by duplicating the test volume as calibrating container and by radiometrically as well as gravimetrically detecting the moisture content, which is varied either by evaporation while the moisture is spread or by adding determined quantities of water.

4 Claims, No Drawings

METHOD FOR CALIBRATING MOISTURE CONTENT MEASURING INSTRUMENTS

BACKGROUND OF THE INVENTION

The present invention relates to a method for calibrating radiometric hygrometers or moisture measuring instruments. The moisture content in loosely piled and heaped material such as coke is presently measured with instruments based on nuclear physics and phenomena. For example, moisture can be determined by using the moderation of fast neutron by hydrogen nuclei (see, for example, Stahl und Eisen, Vol. 82, (1962), pages 1017 to 26). Such a moisture detecting instrument includes a source of neutron radiation such as 241-americium-beryllium and a scintillometer is placed in the immediate vicinity of the source and detector. Source and detector are constructed as probe inside of a protective pipe which, in turn, is placed in the storage facility (container, bin, silo etc.) for the loose moist material. Particularly, the detector is connected to an amplifier and a recorder by means of a special cable.

Upon calibrating this instrument, one usually proceeds as follows. Generally, the instrument is calibrated on basis of otherwise, e.g. empirically available date on the moisture content of the material, gained, for example, by gravimetrically testing such material. Calibrating includes zero offset and gain for the amplification of the detector pulses. The adjustment of zero level and offset includes the instrument parameters as well as the hydrogen content of the material itself, other than in water. Also, the so-called null effect of the probe is induced here.

The instrument characteristics which represent the mathematical relation between instrument incidation and reading on one hand, and the actual moisture content, is determined by determining the moisture content independently, e.g. by gravimetrically analyzing samples. These gravimetric data are then associated with radiometric readings supposedly involving material with the same moisture content as the samples.

The samples are obtained as follows. The container for the loose material is filled so that upon reaching a volume later to be monitored by the calibrated instrument (measuring volume), samples of the material can actually be taken, e.g. through branching off some of the flow and in the order of several pounds material. As the container is filled up to the measuring volume, a reading is taken from the instrument, while the samples are subjected to direct moisture content analysis. Since the mathematical relation between actual moisture content and reading is not umambiguous, many readings, i.e. several hundred readings, spread over several months have to be taken and to be subjected to a regression analysis. These prior art methods and calibration is described by J. Schwarzlose in "Isotope Praxis", 3rd year, 1967, issue 9, the article being entitled "Feuchtemessung an Stuckkoks mit Neutronen" (moisture measurement for lump coke with neutrons) and by J. Luckers, C.N.R.M., No. 11. June 1967 "Continuous Measurement of the Moisture Content of Coke by Means of a Neutron Probe".

In view of the large scattering of the measured values, even a regression analysis will yield only rather vague information of the instrument characteristics. The reason for the ambiguity and scattering of readings lies usually in the method of taking samples. The moisture content of the material is not uniform and upon taking random samples one may have missed that portion which contributes most to the inhomogeneity in the moisture content, but which may significantly influence the radiometric reading. In other words, the samples are not really representative of the moisture content of the measuring volume or of the bin content as a whole. Also of disadvantage is that the measuring points crowd around a medium reading value and are not distributed over the entire measuring range, even though the actual average moisture content in the bin varies. The reason for scattering of the measuring points is also treated in the said two references.

The resulting instrument characteristics was found to be rather unreliable; still, it is then transformed into a calibration curve or calibrated instrument characteristics by means of generally known mathematical and measuring technique methods. This curve is then supposed to represent a definite and exact relation between radiometric moisture detection and the true moisture values, and is transposed upon the test and measuring instrument.

In order to supervise the instrument as to long term stability (drift), one will occasionally run the instrument in a simulated moisture environment (moisture phantom). In order to have a reference available, this simulated environment is established prior to installation of the instrument, i.e., during calibration. One will use here a material such as paraffin wax, a boron paraffin mixture or the like, and the chemical properties thereof will lead to a reading which is separately recorded as a calibration reading to be used as a reference later. The simulated environment is re-established (or maintained) and is used whenever long term drift is to be detected; the reading then obtained is compared with the earlier reference.

This method will yield only one indication as to long term drift of the characteristics as a whole and manifests itself as a parallel shift. Any rotation of the curve will not be detected. One would need here several, at least three such long term reference and calibration points, i.e. one would need correspondingly different simulations. A single phantom condition can yield only one reference point, and cannot be used as standard for calibrating the entire range of the instrument (or of several instruments operating under similar conditions). It was found also that the phantom is actually quite unreliable because that single reference point has about the same degree of uncertainty as the calibration curve itself.

The known methods for calibrating a moisture detecting instrument are, therefor, as follows:
1. The entire procedure is quite time consuming;
2. The procedure must be repeated for each instrument;
3. Sufficiently exact and reliable checks after repairs are lacking;
4. Reproducing results are imperfect, because;
5. the readings scatter, not because of the instrument itself, but because the calibrating samples are not representative for the measuring volume as a whole;
6. The mathematical transformation becomes uncertain when the calibration measurements deviate too much from the final calibration curve;
7. Human errors in taking samples and introduction of subjective errors, particularly when calibration extends over long periods of time.

DESCRIPTION OF THE INVENTION

It is an object of the present invention to provide for a means and improved calibration procedure for moisture detecting instrument using a radiation source and detecting the attenuation of the radiation by moisture in loose material.

In accordance with the preferred embodiment of the invention, a replica of the location of measuring is constructed, for example, as a test container, under the condition that the container has at least the maximum volume of the measuring volume as it will affect the probe. That test point location replica-containing is filled with the same kind of material later to be monitored as to moisture content. Next, the moisture content of that container is varied under controlled conditions and radiometrically detected as well as otherwise to obtain a true representation of the moisture content to be associated with the radiometric reading gained from a neutron source plus detector probe.

In one form of practicing the invention, water is added to the material to moisturize the material completely until water drains and drips off. The detector of the instrument to be calibrated is placed in position and readings are taken while water drips off until the draining ceases, and the moisture content is stabilized actually to the maximum amount the material can hold (saturation). The reading is recorded and will be a stabil value. Immediately thereafter, the material is taken out of the container; while the material is taken out of the container samples are taken for gravimetrically determining the moisture content. That value is then associated with the stabilized instrument reading. The bulk of the material is spread to form a thin layer and let to dry, but not completely. The still moist material is put back into the container, samples are taken and gravimetrically evaluated while an instrument reading is taken, whereupon the material is again taken out, and spread for drying. This procedure is repeated several times until the material is dry. The plural readings are plotted and serve as actual instrument characteristics. That characteristics is then transformed to take different conditions of piling the loose material into consideration to obtain the final, calibrated characteristics.

It was found to be of advantage to increase the time intervals between successive calibration readings in accordance with an e-function because the evaporation of moisture decrease in accordance with such an exponential function. This way, one will obtain almost a straight line as instrument characteristics.

It was found that taking the samples from the spreaded material enhances reliability. The moisture content is quite homogenous as the result of spreading, separation and evaporation. The material is or should be mixed during the procedure of emptying and filling the container.

In most instances, the volume of the material to be supervised, such as the content of a weighing bin, is a large multiple of the volume of the test container, as the volume of the latter is kept to the required minimum in order to facilitate sample taking and to make sure that the material is sufficiently homogenously moist therein.

The difference in volume as between the bin and the test container results in different densities of the heaped material. If the bin is at first only filled to the extent of the calibration volume (test volume of the probe), the instrument reading will change as the bin is filled more and more because the material then under immediate supervision is compressed by the material piled on top. The resulting change in reading is part of the calibration procedure and reflects the change due to compression. That change can be taken into consideration when the measured characteristics is transformed into the calibration characteristics.

As was mentioned above, the conventional method of calibration had as one of its disadvantages that only one point of the phantom reading could be referenced against the instrument characteristics. However, for purposes of long term drift supervision the entire characteristics must be considered and also additional instruments operating under similar conditions should be calibrated analogously but without repeating the procedure of gaining the initial characteristics in each instance. Therefore, a moisture phantom should be used which can be adjusted for simulating the different test values along the characteristics.

This phantom includes different cadmium sheets as neutron absorbing material in which a probe is clad in each instance of obtaining a new reading. Different penetration depth and different wall thicknesses of these absorbing sheets establish particular test values corresponding to the adjustment of the respective instrument in each instance. In other words, the same sheets and similar dispositions define transposable conditions which render readings on different instruments, or of the same instrument but at different times, comparable, and deviations in such readings permit recalibration. Also, different phantom adjustments serve to permit checking on the entire characteristics of the instrument from time to time and permits new adjustment when needed, because of the particular reproducibility of results when using the same (or comparable) absorbing sheets and similar relative disposition in relation to the probe.

The method described above results in a particular test and calibration characteristics and permits correction thereof. However, the method can also be carried out in the reverse. The starting material may be very dry and a first reading is taken. Now, predetermined quantities of moisture are added in steps, and in each instance the measuring container is thoroughly mixed. The gravimetric and radiometric test values are ascertained for each instance of added moisture and the values are mutually associated. The final test point will result from saturation moisturization.

The neutron test method can be used under the following conditions: The content of hydrogen that is part of the chemical composition of the material itself, must be considered, e.g., it must be ascertained separately, and that content must be a known quantity and should remain constant. That content must not enter into the moisture reading and must, therefore, be suppressed.

The material to be investigated must not have chemical elements with an atomic weight less than about ten times the atomic weight of hydrogen (carbon meets that requirement).

The density of the material should remain constant or should be constant on the average, unless compensation is provided for as described.

The invention is not limited to the embodiments described above but all changes and modifications thereof not constituting departures from the spirit and scope of the invention are intended to be included.

We claim:

1. Method of calibrating a radiometrically operating moisture measuring instrument, including a radiation source and a detector in a probe, and signal processing and indicating means, such as recording means external to the probe, for determining the moisture content of loose material such as coke, comprising the steps of:

providing a container having volume at least as large as the volume embraced by the maximum measuring range of the probe;

filling the container with loose material and moisturizing the material in the container beyond saturation, but allowing the material to drain until moisture saturation has stabilized;

taking a radiometric reading of the probe as detecting the moisture content of the material in the container at saturation;

emptying the container and spreading its content to provide a layer of small thickness and permitting uniform evaporation of moisture;

refilling the container and taking a second radiometric reading after having taken at least one sample for gravimetrically determining the moisture content;

repeating the spreading, refilling and instrument reading as well as sample taking and gravimetric determination of the moisture content of the sample, until the material is substantially dry;

providing an associative recording of the gravimetric moisture content determinations and of the instrument readings; and subjecting the recording to further processing to obtain a calibrated instrument characteristics.

2. Method as in claim 1, providing an adjustable moisture phantom for simulating particular moisture values for radiometric measurement and adjusting the phantom to values in accordance with said calibrated characteristics to obtain a reproducible replica of the initial instrument characteristic as calibrated.

3. Method as in claim 1, wherein the sample taking and gravimetrical as well as radiometric readings are taken at increasing time intervals.

4. Method as in claim 1, including gravimetrically determining the moisture content at saturation.

* * * * *